United States Patent [19]

Higa et al.

[11] Patent Number: 5,043,477

[45] Date of Patent: Aug. 27, 1991

[54] METHYL ALLYL TELLURIDE

[75] Inventors: Kelvin T. Higa; Daniel C. Harris, both of Ridgecrest, Calif.

[73] Assignee: The United States of America as represented by the Secretary of the Navy, Washington, D.C.

[21] Appl. No.: 73,248

[22] Filed: Jul. 13, 1987

[51] Int. Cl.[5] .......................................... C07C 395/00
[52] U.S. Cl. ................................................. 562/899
[58] Field of Search ......................... 260/550; 562/899

[56] References Cited

PUBLICATIONS

O'Brien, D. H. et al.; Tellurium-125 and Selenium-77 NMR Shifts for Symmetric and Unsymmetric Diorganyl Chalcogenides, Organometallics, vol. 2, No. 2, pp. 305-307, 1983.

Primary Examiner—John M. Ford
Attorney, Agent, or Firm—Stuart H. Nissim; Donald E. Lincoln; Melvin J. Sliwka

[57] ABSTRACT

The new unsymmetric allyl-(alkyl) telluride compound methyl allyl telluride and other unsymmetric allyl-(alkyl) telluride compounds are prepared by adding an alkyl Grignard to a tellurium/tetrahydrofuran slurry, then subsequent reaction with an alkyl halide. The unsymmetric allyl-(alkyl) telluride product is isolated by filtration followed by vacuum distillation.

1 Claim, No Drawings

METHYL ALLYL TELLURIDE

BACKGROUND OF THE INVENTION

1. Field of the Invention

The present invention is related to metal organic compounds. More particularly, the invention is related to tellurium containing organic compounds and a method for their synthesis.

2. Description of the Prior Art

Metal Organic Chemical Vapor Deposition film growth of Mercury-Cadmium-Telluride (HgCdTe) is adversely affected by the high growth temperatures of 400° C. to 425° C. which are needed to crack diethyl telluride. Problems include mercury evaporation from the film and diffusion across the interface between the film and the substrate. Ditertiarybutyl telluride has been used to deposit CdTe and HgTe films at 250° C. with excellent results. This material has been shown to work at temperatures as low as 220° C. to 230° C. However, the resulting metal films are inadequate for applications in sensitive IR detectors. Furthermore, the preparation of the tellurium source compound, ditertiarybutyl telluride, is a low yield process.

Some unsymmetric dialkyl tellurides are useful as tellurium source compounds in the Metal Organic Chemical Vapor Deposition process. Unsymmetric dialkyl tellurides, phenyl alkyl tellurides and phenyl alkyl selenides have been prepared from the reaction of ditellurides or diphenyl diselenides with organometallic reagents in ether solvent. The present invention does not use ditellurides in the preparation of dialkyl tellurides. This eliminates the need for preparing and isolating ditelluride intermediates.

SUMMARY OF THE INVENTION

A new, unsymmetric allyl-(alkyl) telluride compound has been synthesized and found to be useful as a tellurium source compound in the Metal Organic Chemical Vapor Deposition film growth process. According to the present invention, the new unsymmetric allyl-(alkyl) telluride compound methyl allyl telluride and other unsymmetrical allyl-(alkyl) telluride compounds are prepared by adding an allyl Grignard to a tellurium/tetrahydrofuran slurry and subsequent reaction with an alkyl halide under an inert atmosphere and at temperatures low enough to prevent uncontrolled exothermic reaction. The unsymmetric allyl-(alkyl) telluride product is easily isolated by filtration followed by vacuum distillation.

An object of this invention is the new compound allyl methyl telluride.

Another object of this invention is an efficient, high yield process for preparing allyl methyl telluride and other unsymmetric allyl-(alkyl) telluride compounds.

DETAILED DESCRIPTION OF THE INVENTION

According to the present invention, the new composition of matter allyl methyl telluride is prepared in an efficient process which is also useful for preparing other unsymmetrical allyl-(alkyl) tellurides.

The new compound allyl methyl telluride offers many advantages over previous tellurium source compounds for Metal Organic Chemical Vapor Deposition. It may allow mercury cadmium film growth at temperatures below 180° C. The lower growth temperatures achievable with allyl methyl telluride may reduce or eliminate problems associated with mercury evaporation from the film and diffusion across the interface between the film and the substrate. Additionally, methyl allyl telluride has a better "cracking efficiency" than the best prior materials. That is, processes using methyl allyl telluride as source materials require less source material to deposit the same amount of film.

Methyl allyl telluride is formed under an inert atmosphere and in dark conditions by reaction between an allyl Grignard and a tellurium/tetrahydrofuran slurry, then subsequent reaction with a methyl halide. Methyl allyl telluride is also formed by reaction between a methyl Grignard and a tellurium/tetrahydrofuran slurry, and subsequent reaction with an allyl halide. Alternatively, methyl allyl telluride may be formed by reaction between methyl lithium and a tellurium/tetrahydrofuran slurry, then subsequent reaction with an allyl halide.

Alkyl Grignards other than allyl Grignard may be used to form a variety of unsymmetrical allyl-(alkyl) telluride compounds. The following allyl Grignard compounds work well in the present invention: allyl magnesium bromide, allyl magnesium chloride, and allyl magnesium iodide.

The tellurium/tetrahydrofuran slurry requires cooling to a temperature low enough to prevent an uncontrolled exothermic reaction upon addition of an alkyl halide. Temperatures in the range from about −78° C. to about 0° C. have been found to work well. Temperatures near 0° C. are preferred.

A methyl halide is used in the reaction to form methyl allyl telluride. Other alkyl halides and allyl halides may be used to form a variety of unsymmetric allyl-(alkyl) telluride products. Because the reaction between alkyl halides and alkali metal tellurides is extremely exothermic, addition of an alkyl halide to the mixture must be done slowly. On a ⅓ mole scale, alkyl halide was added at a rate of about 1 mole per hour. Alkyl halides having the formula RX are useful where R is an alkyl selected from the group consisting of methyl, ethyl, n-propyl, iso-propyl, n-butyl, tertiary butyl, and neopentyl; and X is a halide selected from the group consisting of chlorine, bromine and iodine.

Solid and liquid fractions of the reaction mixture were separated by filtration. However, other techniques for separating solids from liquids may be used. The crude product is contained in the liquid fraction. The solid fraction may be extracted with a solvent described above and the extract combined with the liquid fraction. Distilling the combined liquid under an inert gas removes the solvent. The temperature of the distillation should be carried out well below the decomposition temperature of the unsymmetric allyl-(alkyl) telluride compound to be produced. As a result, it may be necessary to carry out the distillation under reduced pressure.

Removal of remaining tetrahydrofuran solvent may be accomplished by forming the azeotrope of pentane and tetrahydrofuran. The azeotrope is created by adding pentane to the liquid remaining from the previous distillation to form an approximately 2:1 volume ratio of pentane to remaining liquid. It is not necessary to isolate a crude product before adding the pentane. Distillation of the azeotrope should be carried out well below the decomposition temperature of the unsymmetric allyl-(alkyl) telluride compound to be produced. As in the first distillation, it may be necessary to carry out the distillation under reduced pressure. Pure methyl allyl telluride was obtained from a crude product by vacuum distillation.

In a typical preparation, an allyl Grignard was added to a stirring tellurium/tetrahydrofuran slurry under an inert atmosphere and dark conditions. After stirring for about 1 hour, the mixture was cooled to 0° C.

A methyl halide was added to the stirring solution held at 0° C. The solution was stirred for about 30 to 60 minutes at 0° C., warmed to room temperature for about 30 minutes and then filtered.

Tetrahydrofuran solvent was distilled off under reduced pressure from about 340 to about 360 mm and at a temperature no greater than 55° C.

Pentane was added to the remaining liquid at an approximately 2:1 volume ratio of pentane to remaining liquid in order to form a low-boiling azeotrope. The pentane/tetrahydrofuran azeotrope was distilled off under argon at a temperature no greater than 55° C. leaving a crude product.

The crude product was vacuum distilled at a pressure of about 8 to 20 mm and at a temperature of no greater than 55° C. to yield pure methyl-(allyl) telluride.

The following example is given to illustrate but not limit the invention:

EXAMPLE

Under an inert atmosphere and dark conditions, a 500 mL flask was charged with 42.8 grams of Te powder and a magnetic stirbar. Approximately 300 mL of dry tetrahydrofuran was added and the stirring tellurium/tetrahydrofuran slurry was cooled to 0° C. Approximately 168 mL of 2M allyl magnesium bromide was added over about 35 minutes. The solution was stirred at 0° C. for about 15 minutes.

Methyl iodide (21 mL) was added over 1 hour. The reaction mixture was stirred for 2 hours at 0° C. The reaction mixture was filtered and the remaining solid fraction was washed with dry tetrahydrofuran. The liquid fractions and washings were combined. Tetrahydrofuran solvent was removed by distillation under argon at reduced pressure and a temperature less than 55° C. Approximately 48.9 grams of crude product was recovered.

Pentane (40 mL) was added to the crude product. A pentane/tetrahydrofuran azeotrope was distilled under argon and at a temperature of 50° C. to 53° C. The vacuum pressure was reduced to about 8 torr and the pot temperature was raised to about 55° C. A final product distilled over a temperature range from 30° C. to 33° C. Approximately 34.4 grams of allyl methyl telluride was collected. This represents a 56% yield.

Elemental analysis for $C_4H_8Te$ is as follows. Calculated: C, 26.15; H, 4.39; Te, 69.46. Found: C, 26.39; H, 4.52; Te, 69.52.

The characteristic nuclear magnetic resonance spectrum is as follows: $^1$H NMR ($d_6$-benzene): $\delta$6.05-5.51 (1H, m), 4.72-4.45 (2H, m), 2.95 (2H, d), 1.55 (3H,s) ppm.

The characteristic $^{13}$C-nuclear magnetic resonance absorption spectrum is as follows: $^{13}$C ($d_6$-benzene): $\delta$137, 114, 5, −21 ppm.

The characteristic $^{125}$Te-nuclear magnetic resonance spectrum (with respect to dimethyl telluride) is 155 ppm.

Modifications and variations of the present invention are possible. It should be understood that, within the scope of the appended claims, the invention may be practiced otherwise than as specifically described.

What is claimed is:

1. The compound methyl-(allyl) telluride.

* * * * *